United States Patent
Xing et al.

(10) Patent No.: US 7,006,921 B1
(45) Date of Patent: Feb. 28, 2006

(54) METHOD FOR ACCURATELY ESTIMATING $PK_A$ OF MOLECULES USING ATOM TYPE DEFINITIONS AND PARTIAL LEAST SQUARES

(76) Inventors: Li Xing, 27 Lansing Ave., Maryland Heights, MO (US) 63043; Rober C. Glen, The Old Grange, Upend, Newmarket, Suffolk CB8 9PH (GB)

( * ) Notice: Subject to any disclaimer, the term of this patent is extended or adjusted under 35 U.S.C. 154(b) by 0 days.

(21) Appl. No.: 09/626,099

(22) Filed: Jul. 26, 2000

Related U.S. Application Data (60) Provisional application No. 60/145,595, filed on Jul. 26, 1999.

(51) Int. Cl.
  *G06F 19/00* (2006.01)

(52) U.S. Cl. .......................................................... 702/19
(58) Field of Classification Search .................. 702/14, 702/19, 27, 31, 22; 435/6
   See application file for complete search history.

(56) References Cited

U.S. PATENT DOCUMENTS

| | | | | |
|---|---|---|---|---|
| 5,751,605 A | * | 5/1998 | Hurst et al. | 364/496 |
| 6,093,691 A | * | 7/2000 | Sivik et al. | 510/515 |
| 6,208,942 B1 | * | 3/2001 | Hurst et al. | 702/27 |

OTHER PUBLICATIONS

Martin, Yvonne C, et al. (Mar. 24–28, 1996) "Use of Semi–Empirical Methods to Predicts the pKa's of Phenols and Anilines: Structures, Statistics, and Solvation." Book of Abstracts, 211th ACS National Meeting. COMP–149, American Chemical Society.*

Barlow, "The Ionization of Morphine, Hydroxyamphetamine and (+)–Tubocurarine Chloride and A New Method for Calculating Zwitterion Constants", Br. J. Pharmac. (1992) vol. 75 pp 50–512.*

Gargallo et al., "Application of multivariate data analysis methods to Comparative Molecular Field Analysis (CoMFA) data: Proton affinities and pKa prediction for nucleic acids components", J. of Computer–Aided Molecular Design vol. 13 (1999) pp. 611–623.*

* cited by examiner

*Primary Examiner*—Marianne P. Allen
(74) *Attorney, Agent, or Firm*—Laurence A. Weinberger (57) ABSTRACT

A computer implemented software method enables the prediction of the $pK_a$ of an arbitrary molecule based upon a knowledge of the molecular structure of that molecule and a statistical analysis of the molecular structures of a group of molecules (training set) for which the $pK_a$ is known. Hierarchical atom connectivity trees are constructed for the training set and the various atoms types identified in each molecule are associated in a bit string for that molecule and also associated with the experimentally determined $pK_a$ for that molecule. PLS analysis of the training set data yields coefficients associated with each atom type represented in the bit strings. A hierarchical atom connectivity tree may then be constructed for the molecule of interest. The predicted $pK_a$ is determined by multiplying the number of occurrences of each atom type in the molecule of interest by the PLS coefficient determined for that atom type and summing the resulting multiplications.

3 Claims, 9 Drawing Sheets

FIGURE 1

Environment Around an Ionizable Center

- E.g. 6-aminoquinoline

Measured 5.6
    predicted 5.0

Start with interesting atom
find connections
find connections to connections
create a tree down to 5 levels
'bin' the atom types for each level
create a 'fingerprint' for this atom

```
Nar          Level 0
 |
Car Car       Level 1
 |    |
Car Car  Car H  Level 2
 |
Car Car       ....
 ....
```

String contains a bin for each required atom type at each level, the number of atom types is accumulated to form the string

FIG. 2

ATOM TYPES

| | | | | |
|---|---|---|---|---|
| C.3 | sp$^3$ carbon | | H | hydrogen |
| C.2 | sp$^2$ carbon | | F | fluorine |
| C.1 | sp$^1$ carbon | | CL | chlorine |
| C.ar | aromatic carbon | | BR | bromine |
| C.cat | cationic carbon | | I | iodine |
| N.3 | sp$^3$ nitrogen | | | |
| N.2 | sp$^2$ nitrogen | | <u>Group Types</u> | |
| N.1 | sp$^1$ nitrogen | | NO$_2$ | |
| N.ar | aromatic nitrogen | | NO | |
| N.am | amide nitrogen | | CN | |
| N.pl3 | planar sp$^3$ nitrogen | | CO | |
| N.4 | protonated sp$^3$ nitrogen | | SO$_2$ | |
| O.3 | sp$^3$ oxygen | | SO | |
| O.2 | sp$^2$ oxygen | | OH | |
| O.CO2 | oxygen in carboxylate and phosphate groups | | | |
| S.3 | sp$^3$ sulfur | | | |
| S.2 | sp$^2$ sulfur | | | |
| S.O | sulfoxide sulfur | | | |
| S.O2 | sulfone sulfur | | | |
| P.3 | sp$^3$ phosphorous | | | |

FIGURE 3

Environment Around an Ionizable Center

- In addition to atom types, certain group types are also used and improve the performance of the algorithm

FIGURE 4

| Atom Type: | C.3 | C.2 | C.1 | C.ar | C.cat | N.3 | N.2 | N.1 | N.ar | N.am | N.pl3 | N.4 | O.3 | O.2 | O.CO2 | S.3 | S.2 | S.O | S.O2 | P.3 | H | F | CL | BR | I | NO2 | NO | CN | CO | SO2 | SO | OH |
|---|---|---|---|---|---|---|---|---|---|---|---|---|---|---|---|---|---|---|---|---|---|---|---|---|---|---|---|---|---|---|---|---|
| Level 0 | | | | | | | | | | | | | | | | | | | | | | | | | | | | | | | | |
| Level 1 | | | | 2 | | | | | 1 | | | | | | | | | | | | | | | | | | | | | | | |
| Level 2 | | | | 3 | | | | | | | | | | | | | | | | | | | | | | | | | | | | |
| Level 3 | | | | 3 | | | | | | | | | | | | | | | | | 1 | | | | | | | | | | | |
| Level 4 | | | | 1 | | | | | | | 1 | | | | | | | | | | 2 | | | | | | | | | | | |
| Level 5 | | | | | | | | | | | | | | | | | | | | | 3 | | | | | | | | | | | |

FIGURE 5

| Atom Type: | C.3 | C.2 | C.1 | C.ar | C.cat | N.3 | N.2 | N.1 | N.ar | N.am | N.pl3 | N.4 | O.3 | O.2 | O.CO2 | S.3 | S.2 | S.O | S.O2 | P.3 | H | F | CL | BR | I | NO2 | NO | CN | CO | SO2 | SO | OH |
|---|---|---|---|---|---|---|---|---|---|---|---|---|---|---|---|---|---|---|---|---|---|---|---|---|---|---|---|---|---|---|---|---|
| Level 0 |  |  |  |  |  |  | 1 |  |  |  |  |  |  |  |  |  |  |  |  |  |  |  |  |  |  |  |  |  |  |  |  |  |
| Level 1 |  | 2 |  |  |  |  |  |  |  |  |  |  |  |  |  |  |  |  |  |  |  |  |  |  |  |  |  |  |  |  |  |  |
| Level 2 |  | 1 |  |  |  |  |  |  |  |  |  |  |  |  |  |  |  |  |  |  | 2 |  |  |  |  |  |  |  |  |  |  |  |
| Level 3 | 1 |  |  |  |  |  |  |  |  |  | 1 |  |  |  |  |  |  |  |  |  | 1 |  |  |  |  |  |  |  |  |  |  |  |
| Level 4 | 1 |  |  |  |  |  |  |  |  |  |  |  |  |  |  |  |  |  |  |  | 2 |  |  |  |  |  |  |  |  |  |  |  |
| Level 5 |  |  |  |  |  | 1 |  |  |  |  |  |  |  |  |  |  |  |  |  |  | 1 |  |  |  |  |  |  |  |  |  |  |  |

FIGURE 6

No. of atoms of certain type at each level

| | N.ar | C.ar | H | N.pl3 |
|---|---|---|---|---|
| Level 0 | 1 | | | |
| Level 1 | | 2 | | |
| Level 2 | | 3 | 1 | |
| Level 3 | | 3 | 2 | |
| Level 4 | | 1 | 3 | |
| Level 5 | | | | 1 |

Construction of the hierarchical tree from one example, 6-amino quinoline

Prediction on Molecules

- 37 acid and base molecules selected by Perrin* et al. as examples, and were not included in the training set
- For molecules containing multiple ionizable centers the model correctly predicted the order for all of them, ie

*Perrin DD, Dempsey B, Serjeant EP, *pKa prediction for organic acids and bases*, Chapman and Hall, London, 1981.

US 7,006,921 B1

METHOD FOR ACCURATELY ESTIMATING PK$_A$ OF MOLECULES USING ATOM TYPE DEFINITIONS AND PARTIAL LEAST SQUARES

Benefit of U.S. Provisional Application No. 60/145,595 filed Jul. 26, 1999 is hereby claimed. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates to the calculation from the molecular structure of the pK$_a$ of molecules which contain an ionizable group. More specifically, the pK$_a$ is estimated by applying the coefficients derived by the PLS (Partial Least Squares) statistical methodology from a training set of compounds with known pK$_a$s to the hierarchical connectivity characteristic of the molecule of interest.

BACKGROUND OF THE INVENTION

The bio-availability of a drug to the therapeutic target is an important consideration in rational drug design. Before a drug elicits an effect, it has to pass through various cellular barriers either by passive diffusion and/or by carrier-mediated uptake. Depending on the location of the target site, the pH of the environment may vary considerably. Many molecules of biological interest contain acidic and/or basic groups which govern their biological properties. In particular, the ability of molecules to cross biological membranes is governed in part by the ionization state of the molecule in the pH of the surrounding medium. The proportion of neutral and charged molecular species present at a given pH is determined by the pK$_a$ value. The pK$_a$ can be determined by laborious and detailed measurements or by an empirical system of estimation developed over the years by Perrin et. al. With the advent of combinatorial synthesis and high throughput screening, the number of molecules for which it is desirable to know the pK$_a$ far exceeds the ability to synthesize the molecules and experimentally determine the pK$_a$.

SUMMARY OF THE INVENTION

What has been needed for some time is a simple, fast, and reliable method to estimate pK$_a$ with a high degree of accuracy for any molecule including molecules with more than one ionizable moiety. The present invention accomplishes the estimation of pK$_a$ with such accuracy and speed. Using the idea that the degree of ionization of a particular group depends upon its sub-environment (which is comprised of the neighboring atoms and bonds), a hierarchical tree may be constructed from the ionizing atom outwards. This tree contains atoms directly connected to the root atoms at the first level, those bonded to the first level at the second level, and so on. The estimation of pK$_a$ is accomplished by constructing for each molecule in a training set the hierarchical tree and applying the Partial Least Squares statistical methodology as implemented in the SYBYL software program to this group of molecules for which a measured pK$_a$ is available to extract predictive coefficients.

DETAILED DESCRIPTION OF THE INVENTION

Figure 1:
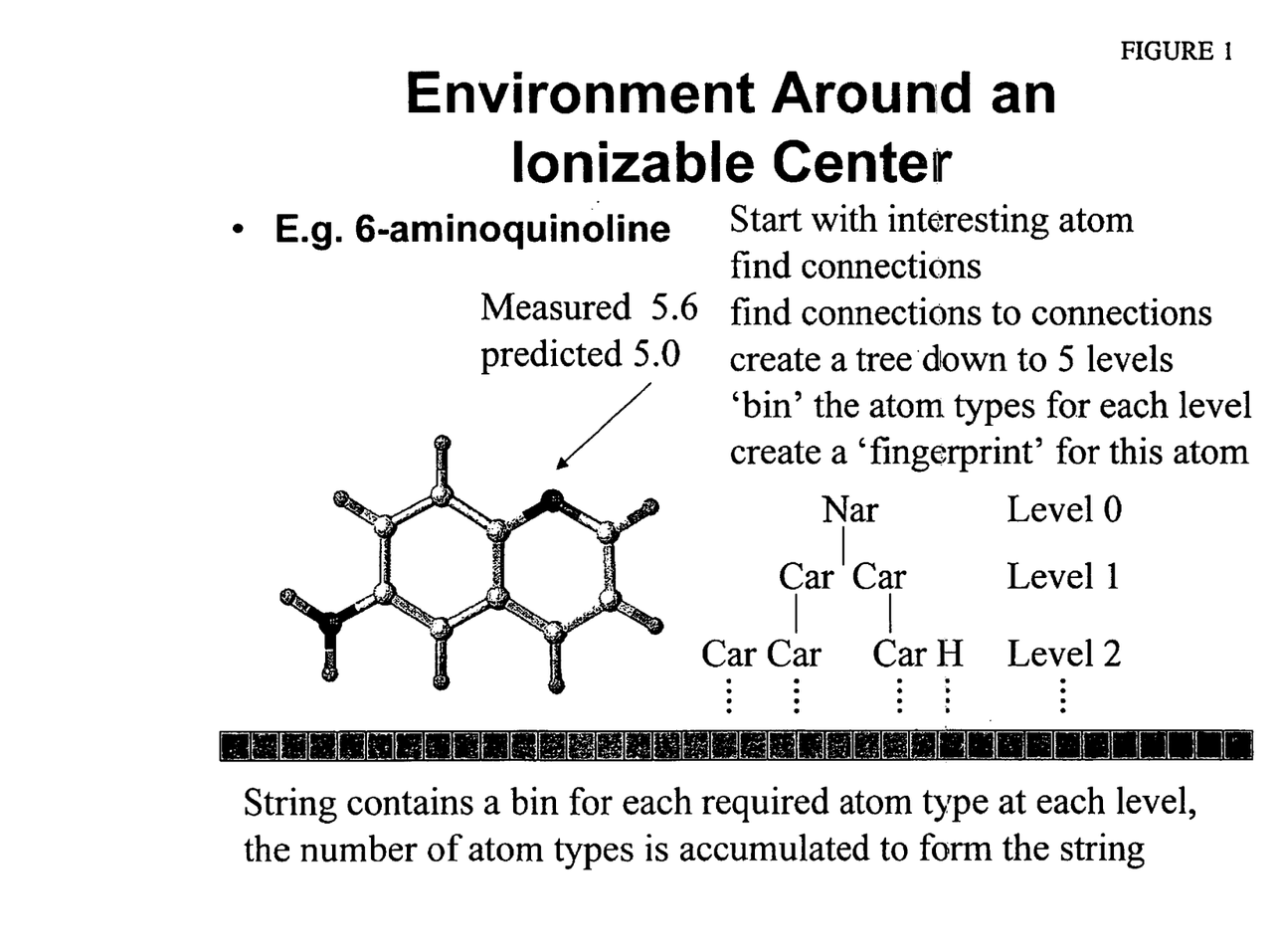
FIG. 1 schematically outlines the procedure for determining a hierarchical connectivity definition for a molecule starting from an ionizable center.

For each molecule in the training set group, a hierarchical tree of atom connectivities found in the molecule is constructed, starting from an ionizable center, which reflects the atom types at each level of connectivity. The overall procedure is schematically indicated in FIG. 1. Since each of the molecular hierarchical connectivity definitions is associated with a measured pK$_a$, the system is complex and a statistical methodology must be used to extract a predictive model. Depending on the size of the training sample, the system may be over determined or under determined. The result of applying PLS to a group (training set) of molecules is the determination of coefficients associated with each atom type at each of the hierarchical levels which reflects the contribution of that atom type at that level to the final pK$_a$. To predict the pK$_a$ for a molecule not included in the original group, the atom type connectivity for that molecule is determined and for each bin the number of occurrences of the atom type in the bin is multiplied by the corresponding PLS determined coefficient for that bin. The sum of the individual bin multiplications over all the bins is the predicted pK$_a$.

Figure 2:
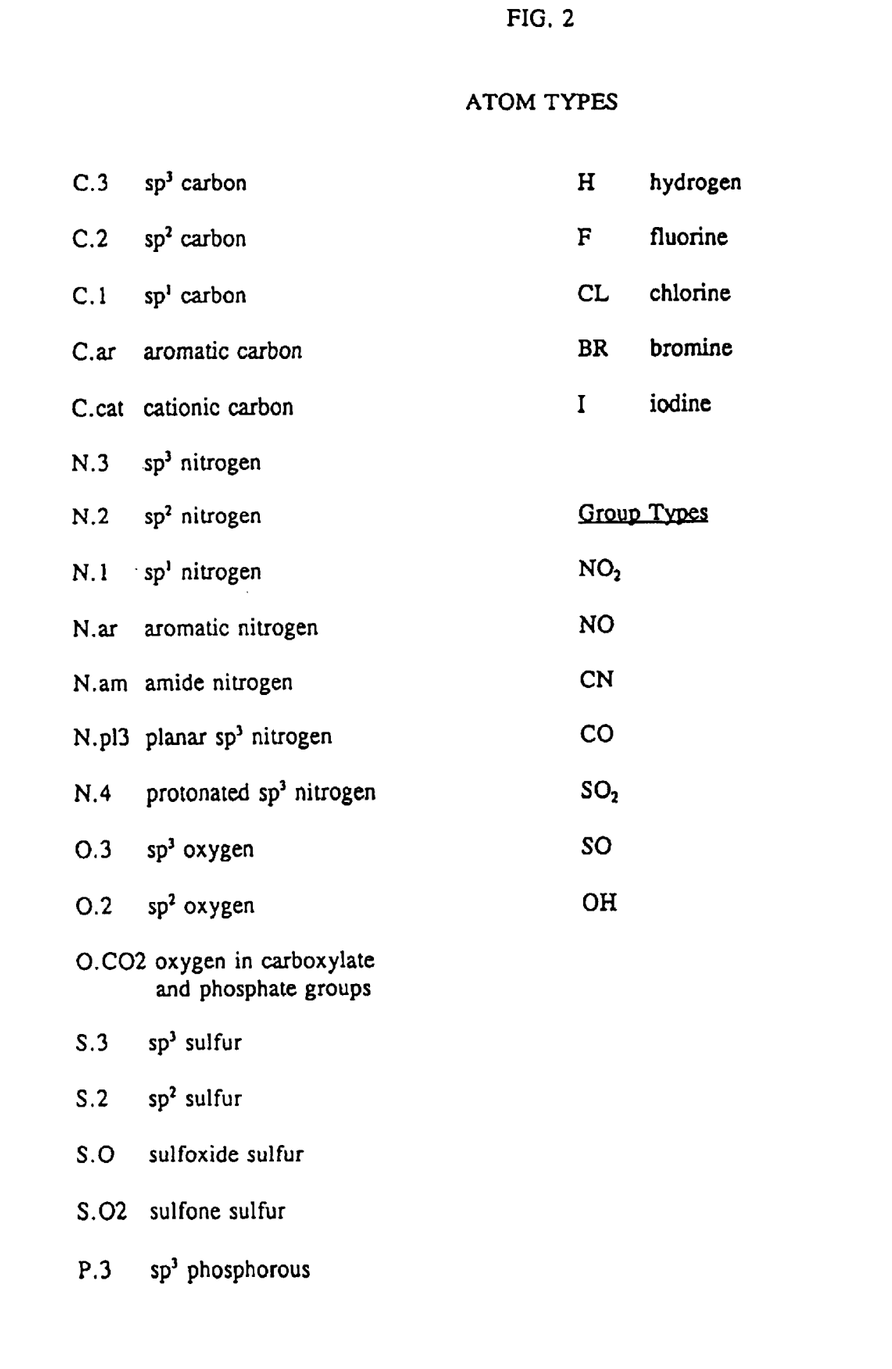
FIG. 2 is a list of typical atom and group type definitions used to construct the hierarchical connectivity definition for a molecule.
Figure 3:
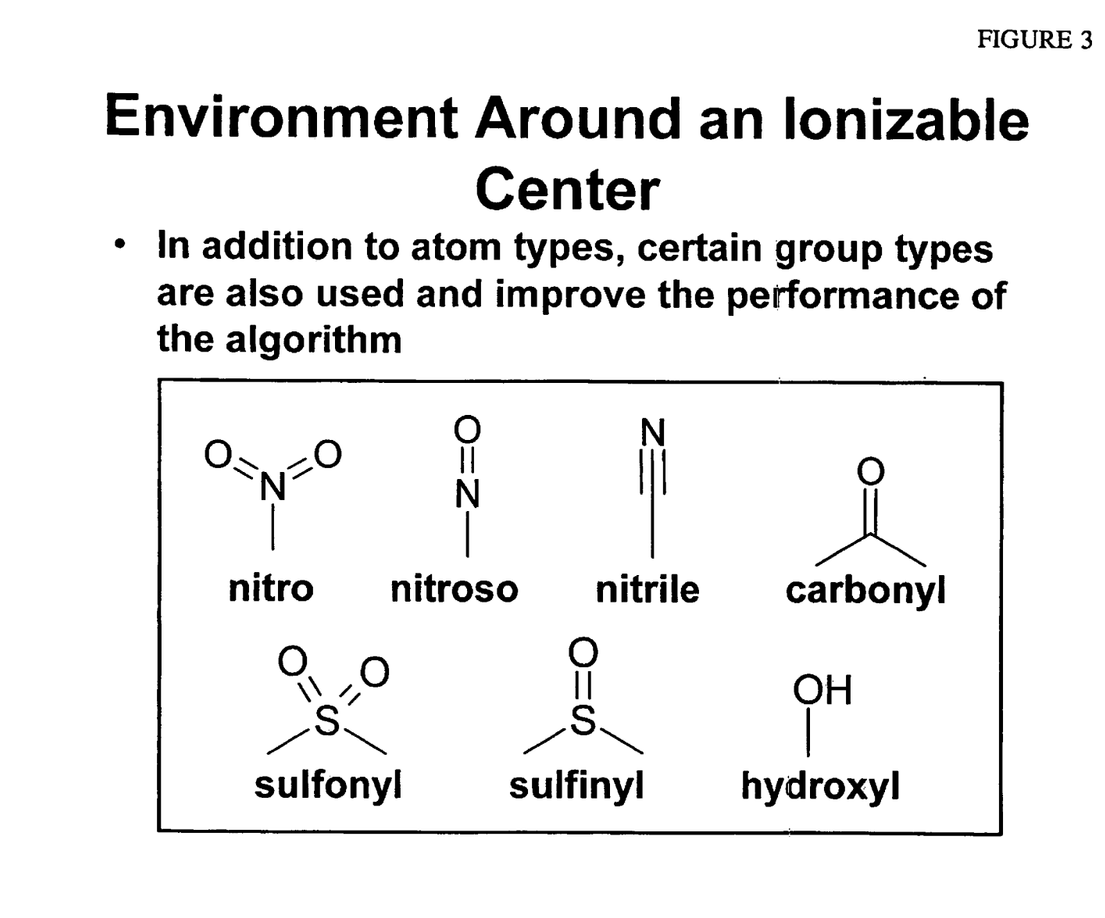
FIG. 3 shows a molecular representation of the group type definitions of FIG. 2.
Figure 4:
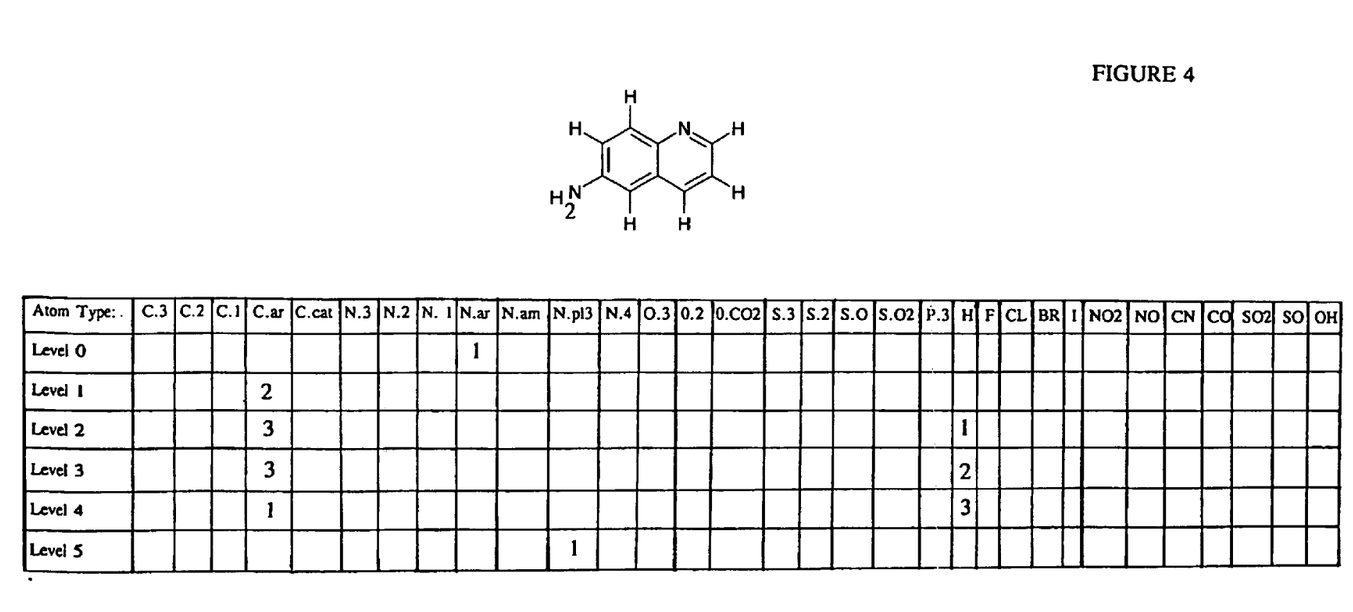
FIG. 4 shows how the hierarchical connectivity definition for 6-amino quinoline is placed within a table of levels of atom connectivity and group type definitions.
Figure 5:
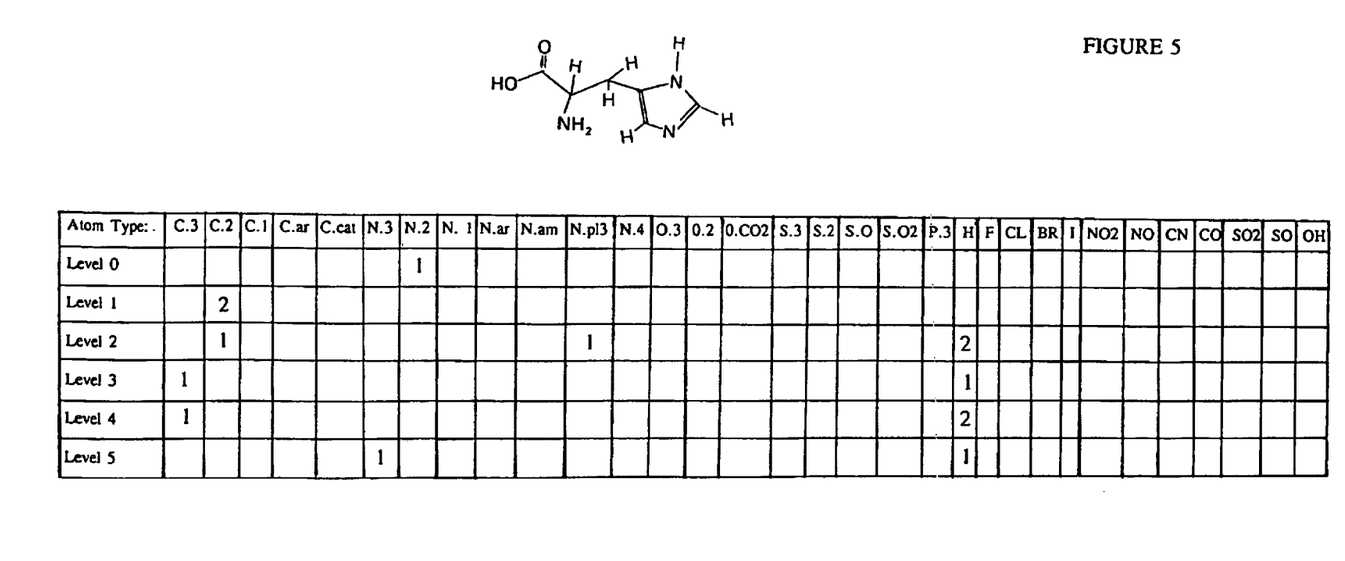
FIG. 5 shows how the hierarchical connectivity definition for an imidazole is placed within a table of levels of atom connectivity and group type definitions.
Figure 6:
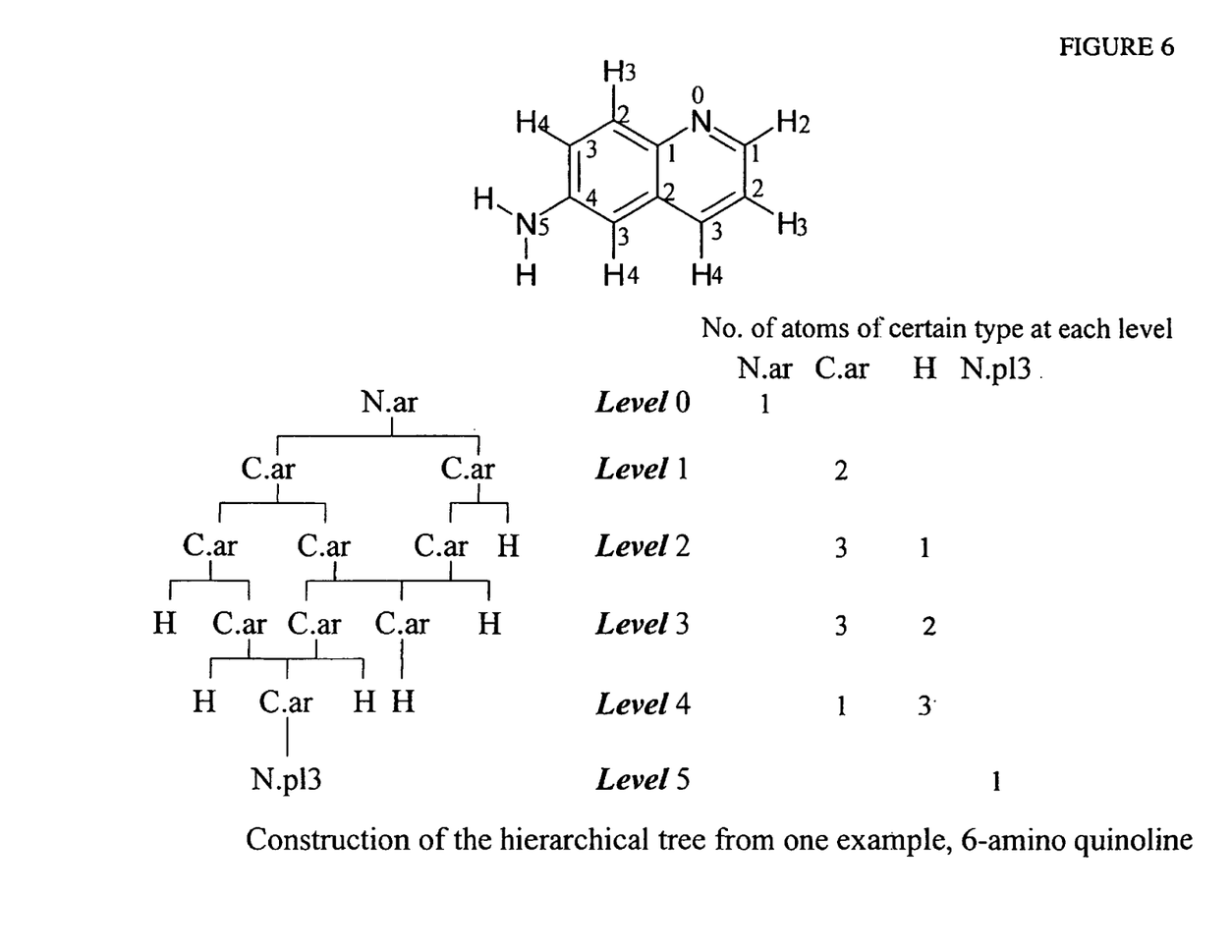
FIG. 6 shows how the hierarchical connectivity tree is defined for 6-amino quinoline.

Many different atom type definitions may be used, but the inventors have found the types set out in FIG. 2 to be most useful. 25 atom types are defined along with 7 group types. The group types are also shown in FIG. 3. Most molecules of biological interest can be defined with these 32 types. Examples for defining the atom type connections for two molecules are shown in FIG. 4 and FIG. 5. At each level, the number of times each atom type occurs at that level is noted in the appropriate "bin." Thus, for 6-amino quinoline, shown in FIG. 4 and FIG. 6, the ionizable nitrogen of interest is defined as an aromatic nitrogen at level 0. Level 1 includes the two aromatic carbons attached to the level 0 nitrogen. Level 3 finds one hydrogen attached to an aromatic carbon, and three different aromatic carbons. This process of definition may be continued for as many additional hierarchical levels as desired. The inventors have found that 5 levels beyond the initial zero level produce very good results. Using the atom type definitions found in FIG. 2, 32 possible atom type bins are available at each level. However, for level 0, only 20 bins are necessary since the tree would never start with hydrogen, halogens, or group types. The maximum number of bins which could be used for the atom type definitions set out in FIG. 2 would be [(5×32)+20]=180. Clearly, for other atom type definitions, a greater or lesser number of bins could be used to form the molecular "fingerprint". Also, if a particular atom type does not occur in the training sample, that atom type will be excluded from further use. One of the interesting properties of the method of this invention is that it can still predict with reasonable accuracy the $pK_a$ of a molecule which has an atom type within it which was not found in the training sample. Typically, only approximately 50% of the atom types may be found in a training sample.

Figure 7:
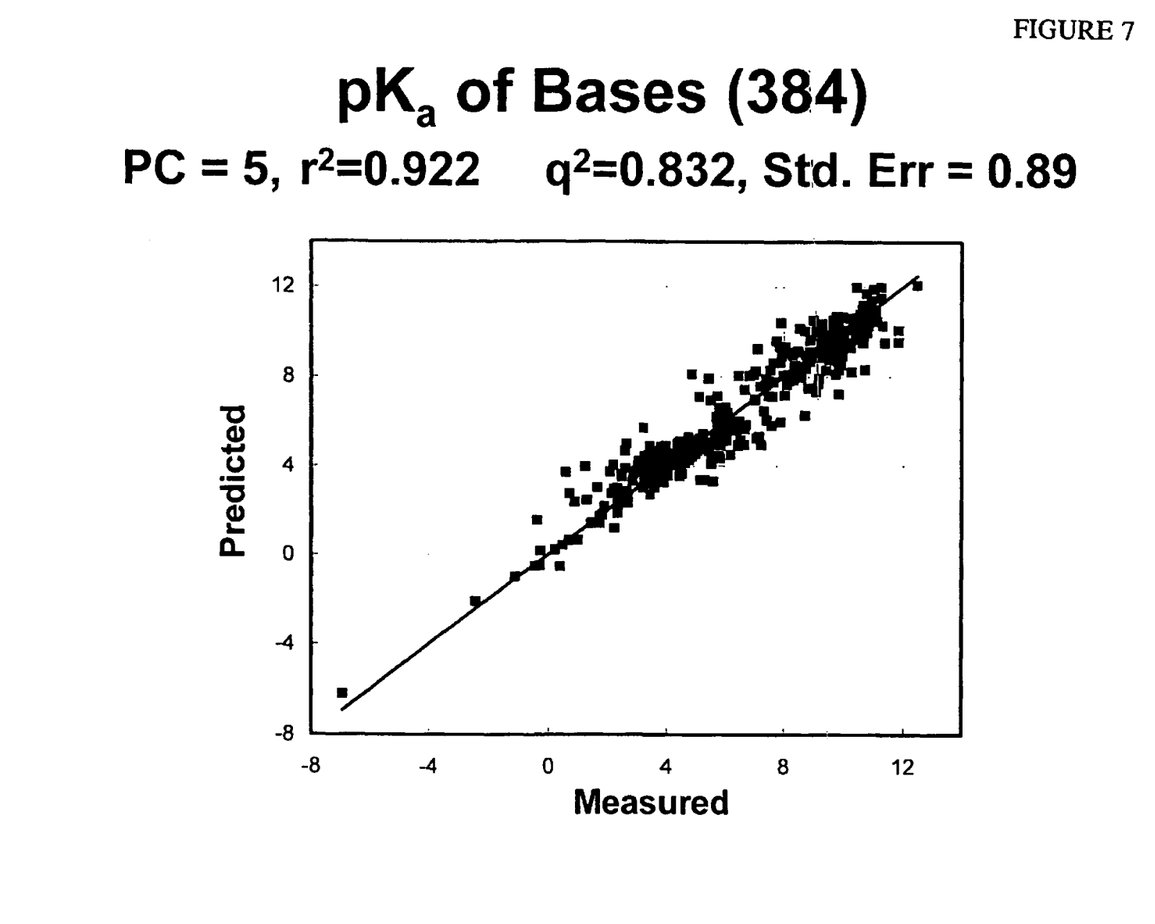
FIG. 7 shows a scatter plot of predicted versus measured values for the pK$_a$ of bases.
Figure 8:
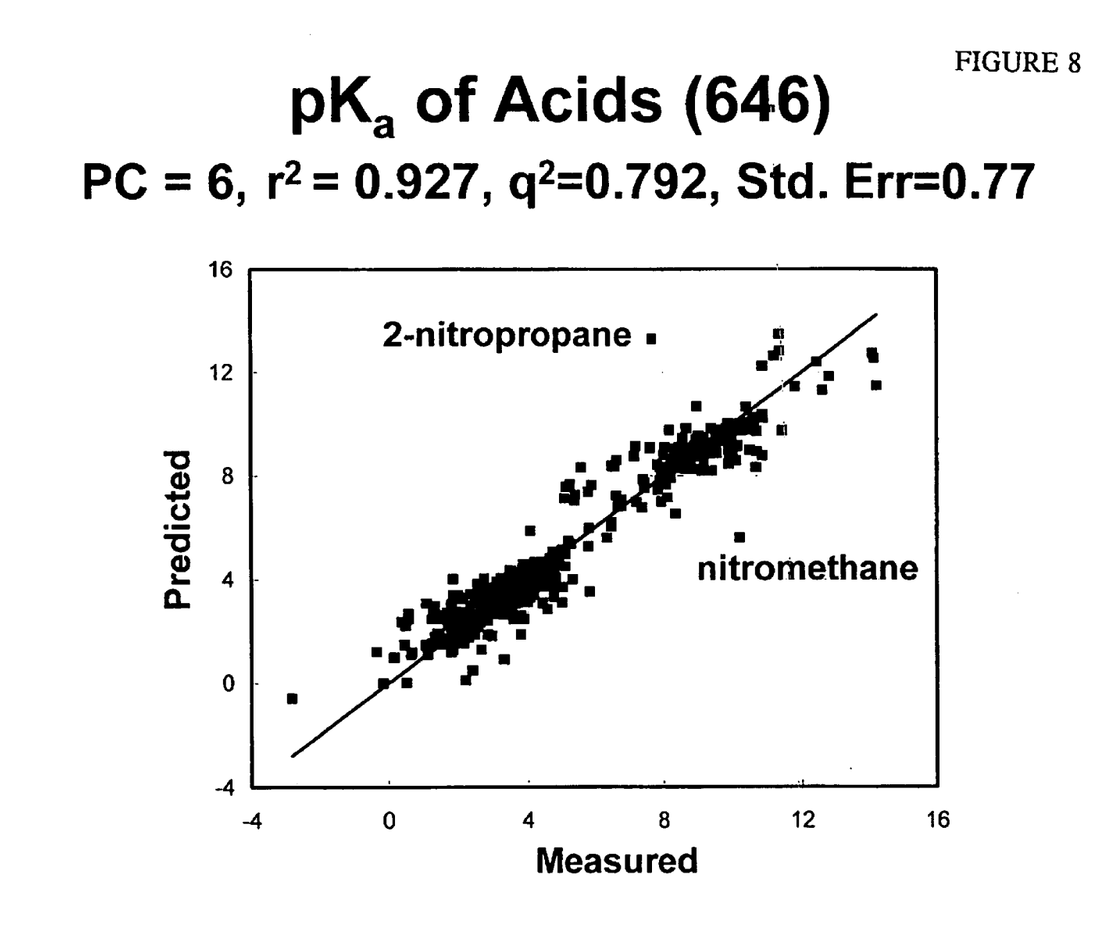
FIG. 8 shows a scatter plot of predicted versus measured values for the pK$_a$ of acids.

Once the fingerprints for all molecules in the initial training group have been determined, the fingerprints along with the measured $pK_a$ for each molecule are analyzed with PLS using a cross-validation procedure. Generally, when using PLS, a sufficient number of components are extracted to yield a cross-validated $q^2$ of at least 0.5. As can be seen in FIG. 7, when 384 bases were used in the training sample, 5 principal components yielded a $q^2$ of 0.832. As shown in FIG. 8, a sample of 646 acids using 6 principal components yielded a $q^2$ of 0.792. These results are statistically significant. Further, the scatter plots shown in FIG. 7 and FIG. 8 clearly demonstrate that the method is highly predictive. The solid line represents the ideal correlation between predicted and measured values. The predictive values shown are the result of the PLS analysis.

Figure 9:
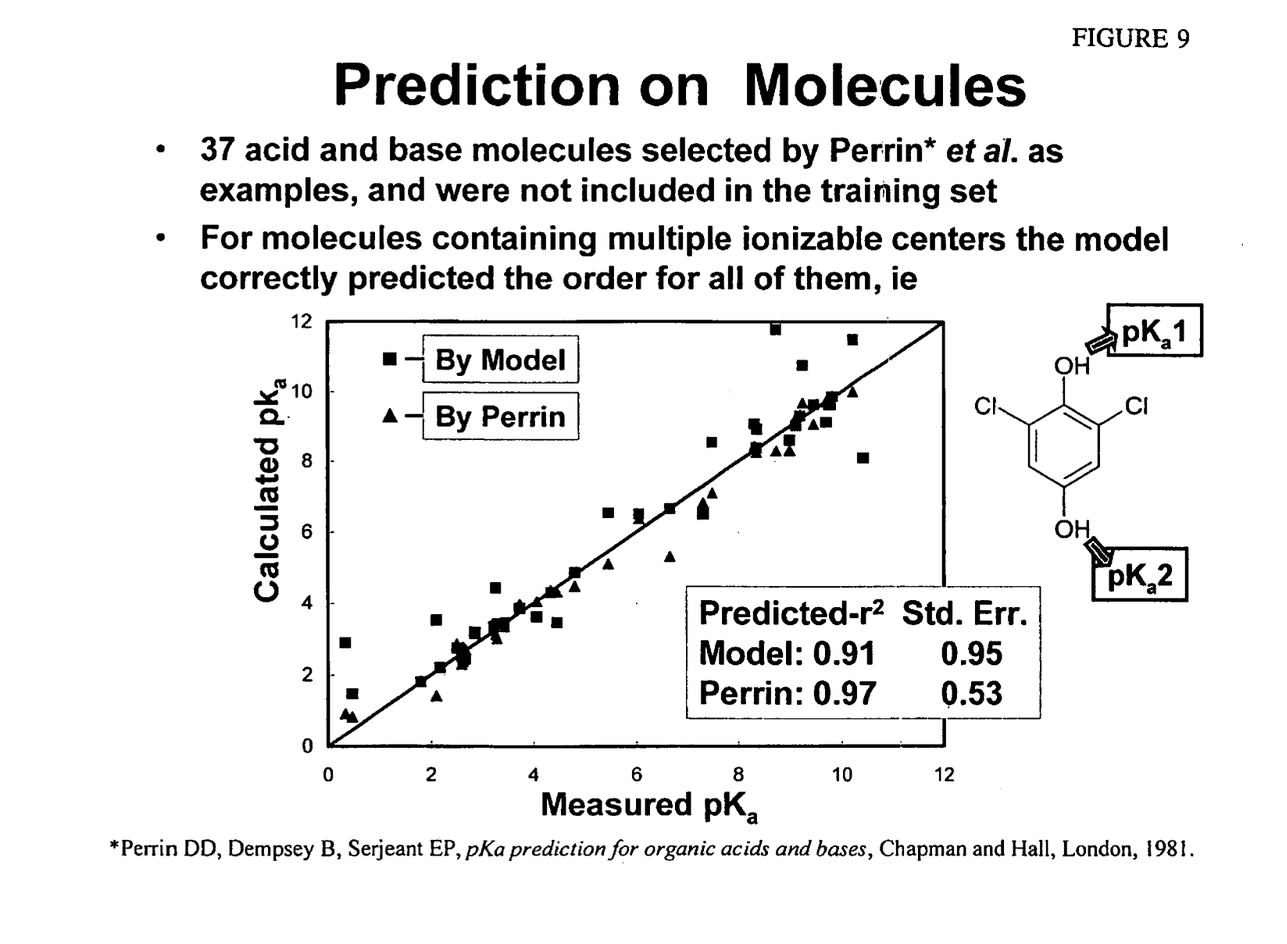
FIG. 9 shows a scatter plot of the predicted versus measured values of 37 compounds which were not included in the training set for the method of the present invention. Two sets of predicted values are shown, those derived by the method of the present invention and those derived by the method of Perrin.

As noted, the result of using PLS with the training sample is the generation of a coefficient for each of the bins which reflects the contribution of the atom type in that bin to the total $pK_a$. For the imidazole shown in FIG. 5, multiplying the number of occurrences of each atom type in the hierarchial definition by the coefficient determined by PLS for each bin and summing the result, yields a predicted $pK_a$ of 6.63. This corresponds well to the measured $pK_a$ of 6.04. Predicted versus measured $pK_a$s using the method of Perrin and the method of this invention are set out in Table 1 and as a scatter plot in FIG. 9.

The coefficients found from the training sample by PLS will, of course, vary somewhat with the molecules in the training sample. However, for a sufficiently large and diverse training sample, such variation will be minimal. The method of this invention thus allows the simple, rapid, and highly accurate determination of the $pK_a$ for any molecule of interest.

All computations including the hierarchical connectivity definitions, the PLS analysis, and the PLS prediction are implemented in a modern computational chemistry environment using software designed to handle molecular structures and associated properties and operations. For purposes of this Application, such an environment is specifically referenced. In particular, the computational environment and capabilities of the SYBYL software program As developed and marketed by Tripos, Inc. (St. Louis, Mo.) is specifically utilized. The software script written in SPL (SYBYL Programming Language) to implement the functionality of the disclosed method is provided in an Appendix to this Application. Software with similar functionalities to SYBYL is available from other sources, both commercial and non-commercial, well known to those in the art. In addition to SYBYL, other commercial software packages are available to implement PLS. A general purpose programmable digital computer with ample amounts of memory and hard disk storage is required for the implementation of this invention.

TABLE 1

| Name | Structure | Perrin | Model | Measured | Comment |
|---|---|---|---|---|---|
| Prediction of pKa values of substituted aliphatic acids and bases: | | | | | |
| Acid strengthening: $-\Delta$ pKa = 0.06 + 0.63 $\sigma^*$ | | | | | |
| Base-weakening: $-\Delta$ pKa = 0.28 + 0.87 $\sigma^*$ | | | | | |
| Bis(2-chloroethyl)(2-methoxyethyl)amine | | 5.10 | 6.54 | 5.45 | |
| 1-(4'-hydroxycyclohexyl)-2-(isopropylamino)-ethanol | | 9.99 | 11.49 | 10.23 | PKa for amino |

TABLE 1-continued

| Name | Structure | Perrin | Model | Measured | Comment |
| --- | --- | --- | --- | --- | --- |
| 2-aminocycloheptanol | | 9.67 | 10.75 | 9.25 | PKa for amino |
| N,N-dimethyl-2-butyn-1-amine | | ~8.1 | 10.44 | 8.28 | |
| 5-amino-3-azapentanol | | 9.87 | 9.85 | 9.82 | PKa1: 5-amino; pKa2: 3-azo Predicted pKa2: 9.29 |
| 5-chloro-3-methyl-3-azapentanol | | 7.1 | 8.53 | 7.48 | PKa for amino |
| Hexamethylenetetramine | | ~6.0 | 11.35 | 6.2 | |
| 2-acetylbutanedioic acid | | 3.15 | 3.19 | 2.86 | PKa1: 1-COOH; pKa2: 4-COOH Predicted pKa2: 3.68 |
| Methionine | | 2.20<br>9.33 | 2.20<br>9.29 | 2.17<br>9.20 | PKa1: COOH<br>PKa2: amino |
| Piperazine | | 9.85 | 9.61 | 9.78 | |
| The Taft equation: pK = pK$^0$ − ρ*Σ(σ*) | | | | | |
| 2-(methylamino)-acetamide | | 8.43 | 9.07 | 8.31 | PKa for amino |
| 2-(dimethylamino)-ethyl acetate | | 8.26 | 8.38 | 8.35 | PKa for amino |
| 2,3-dihydroxy-2-hydroxymethylpropanoic acid | | 3.01 | 3.42 | 3.29 | Pka for COOH |
| 1,8-diamino-3,6-dithiaoctane | | 9.06 | 9.62 | 9.47 | |
| Chlorodifluoroacetic acid | | 0.82 | 1.47 | 0.46 | |
| Mopholine | | 8.92 | 8.92 | 8.36 | |

TABLE 1-continued

| Name | Structure | Perrin | Model | Measured | Comment |
|---|---|---|---|---|---|
| 4-morpholino-2,2-diphenylpentanenitrile | | 6.38 | 6.51 | 6.05 | |

Prediction of pKa values for phenols, aromatic carboxylic acids and aromatic amines
The Hammett equation: $pKa = pKa^0 - \rho(\Sigma\sigma)$

| Name | Structure | Perrin | Model | Measured | Comment |
|---|---|---|---|---|---|
| 4-chloro-3,5-dimethylphenol | | 9.70 | 9.11 | 9.71 | |
| Pyrogallol | | 9.24 | 9.02 | 9.12 | PKa1: 1- or 3-OH; Pka2: 2-OH<br>Predicted pKa2: 9.54 |
| Benzenehexol | | 8.31 | 8.60 | 9.0 | |
| Picric acid | | 0.91 | 2.89 | 0.33 | |
| 2,6-dichloro-1,4-benzenediol | | 6.82 | 6.50 | 7.30 | PKa1: 1-OH; pKa2: 4-OH<br>Predicted pKa2: 7.85 |
| 3,4,5-trihydroxybenzoic acid | | 4.32 | 3.46 | 4.46 | PKa1: COOH; pKa2: 3- or 5-OH; pKa3: 4-OH<br>Predicted pKa2: 8.80, pKa3: 9.47 |

TABLE 1-continued

| Name | Structure | Perrin | Model | Measured | Comment |
|---|---|---|---|---|---|
| 4-bromo-1,2-benzenedicarboxylic acid | | 2.86 | 2.74 | 2.5 | PKa1: 2-COOH; pKa2: 1-COOH Predicted pKa2: 3.48 |
| 4-hydroxy-3,5-dimethoxybenzoic acid | | 4.36 | 4.30 | 4.34 | PKa1: COOH; pKa2: 4-OH Predicted pKa2: 7.13 |
| 3-iodo-4-methylthioaniline | | 3.34 | 3.44 | 3.44 | |
| 4-bromo-3-nitroaniline | | 1.82 | 1.80 | 1.80 | |

Prediction of pKa values of heteroaromatic acids and bases by the Hammett and Taft equations.

| Name | Structure | Perrin | Model | Measured | Comment |
|---|---|---|---|---|---|
| 3-acetylpyridine | | 3.13 | 4.43 | 3.26 | |
| 3-bromo-5-methoxypyridine | | 2.30 | 2.50 | 2.60 | |
| 3-hydroxypyridine | | 4.48<br>8.29 | 4.86<br>11.78 | 4.80<br>8.74 | |
| 4-aminopyridazine | | 5.31 | 6.66 | 6.65 | PKa1: 1-N; pKa2: 2-N Predicted pKa2: 3.64 |

TABLE 1-continued

| Name | Structure | Perrin | Model | Measured | Comment |
|---|---|---|---|---|---|
| 4-amino-6-chloropyrimidine | | 1.41 | 3.52 | 2.10 | PKa1: 3-N; pKa2: 1-N Predicted pKa2: 1.30 |
| Extension of the Hammett and Taft equations to heterocycles. | | | | | |
| 4-nitrothiophen-2-carboxylic acid | | 2.70 | 2.44 | 2.68 | |
| 4-bromopyrrol-2-carboxylic acid | | 4.05 | 3.62 | 4.06 | PKa for COOH |
| Furan-2,4-dicarboxylic acid | | 2.77 | 2.37 | 2.63 | PKa1: 2-COOH; pKa2: 4-COOH Predicted pKa2: 3.58 |
| Pyrazole-3-carboxlylic acid | | 3.98 | 3.86 | 3.74 | PKa for COOH |
| 1,2,3-triazole-4-carboxylic acid | | 3.25 | 3.35 | 3.22 | PKa for COOH |

APPENDIX

```
@macro predict_pka sybylbasic
lookahead $*
# atom type list
setvar atype_list C.3 C.2 C.1 C.ar C.cat N.3 N.2 N.1 N.ar N.am N.p13 N.4 \
        O.3 O.2 O.co2 S.3 S.2 S.o S.o2 P.3 H F Cl Br I
setvar group_list NO2 NO CN CO SO2 SO OH NH2c NH2r
setvar simple_types H,F,CL,BR,I
# bond type list
#setvar btype_list 1 2 3 AM AR
# atype list for the 0th level
# setvar Ntype_list N.3 N.2 N.1 N.ar N.am N.p13 N.4
setvar Ntype_list C.3 C.2 C.1 C.ar C.cat N.3 N.2 N.1 N.ar N.am \
  N.p13 N.4 O.3 O.2 O.co2 S.3 S.2 S.o S.o2 P.3 H F Cl Br I
# the atom that is ionized has to be numbered "1"
#setvar N_atom 1
# N_LEVELS has to be same as that used for pls model
# setvar N_LEVELS %prompt(INT 5 "Enter the level of tree" "No of layers \
# to consider as effectors of pKa of root atom")
setvar N_LEVELS 5
# prompt if molecule is represented by Sybyl or Unity atom types
setvar sybyl_or_unity %prompt( string "SYBYL" "SYBYL or UNITY"\
        "Is the molecule represented by Sybyl or Unity atom types?")
# prompt if predicting for bases or acids
setvar acid_or_base %prompt( string "BASE" "ACID or BASE"\
        "Is the acid or base you want to predict pka for?")
if %streql( %uppercase( %substr($acid_or_base 1 1) ) B )
    if %streql( %uppercase( %substr($sybyl_or_unity 1 1) S)
        setvar pls_file "/home5/lxing/pka/predict_pka/bases/new/bases_sybyl.lis"
```

APPENDIX-continued

```
        else
            setvar pls_file "/home5/lxing/pka/predict_pka/source/unity/bases_unity.lis"
        endif
    else
        if %streql( %uppercase( %substr($sybyl_or_unity 1 1) S)
            setvar pls_file "/home5/lxing/pka/predict_pka/acids/new/acids_sybyl.lis"
        else
            setvar pls_file "/home5/lxing/pka/predict_pka/source/unity/acids_unity.lis"
        endif
endif
setvar fhdr %open( $pls_file r)
# prompt for mol area for prediction
setvar mol_area %prompt( m_exp "" "MOLECULES"\
            "select molecular areas for prediction")
setvar old_default $default_area
for ma in %mols( $mol_area)
default $ma > $nulldev
setvar atom_pick %prompt( a_exp "" "Atoms" "Pick the atoms for prediction" )
for N_atom in %atoms( $atom_pick)
# initialize variables
    for j in $Ntype_list
        setvar a_count[0][$j] 0
    endfor
    for i in %range(1 $N_LEVELS)
        for j in $atype_list
            setvar a_count[$i][$j] 0
        endfor
        for j in $group_list
            setvar g_count[$i][$j] 0
        endfor
        setvar atoms_at_level[$i]
    endfor
    setvar one_more_level %math( $N_LEVELS + 1 )
    setvar atoms_at_level[$one_more_level]
# record the zeroth level
    setvar atype % atom_info( $N_atom type )
    setvar a_count[0][$atype] 1
# "$passed_set" is a set containing all the atom id's having been traversed
    setvar passed_set $N_atom
    setvar ngh %atom_info( $N_atom neighbors )
    for k in $ngh
        if %not( %set_member($k $passed_set) )
            setvar atoms_at_level[1] $atoms_at_level[1] $k
#           setvar parent[$k] $N_atom
            setvar passed_set %set_or($passed_set $k)
        endif
    endfor
# loop until N_LEVELS is reached
    setvar level 1
    while %lteq( $level $N_LEVELS )
        setvar next_level %math($level + 1)
        for j in $atoms_at_level[$level]
            setvar atype %atom_info( $j type )
            setvar find_group
            switch $atype
amino NH2 (alkyl) group
            case N.3)
                setvar ngh %atom_info( $j neighbors )
                setvar ngh_left %set_diff( %set create($ngh) $passed_set )
                setvar count_H
                for ngh in %set_unpack( "$ngh_left" )
                    setvar ngh_atype %atom_info( $ngh type)
                    if % streql( $ngh_atype H)
                        setvar count_H %set_or("$count_H" $ngh)
                    endif
                endfor
                if %eq( %set_size("$count_H") 2 )
                    setvar passed_set % set_or( $passed_set $count_H )
                    setvar g_count[$level][NH2c] %math( $g_count[$level][NH2c] + 1 )
                    setvar find_group TRUE
                endif
                ;;
            case N.p13)
                setvar ngh %atom_info( $j neighbors )
                setvar ngh_left %set_diff( %set create($ngh) $passed_set)
amino NH2 (aryl) group
                setvar count_H
nitro NO2 group (Sybyl format)
                setvar count_O
```

APPENDIX-continued

```
            for ngh in %set_unpack( "$ngh_left" )
                setvar ngh_atype %atom_info( $ngh type )
                if %streql( $ngh_atype H )
                    setvar count_H % set_or("$count_H" $ngh)
                endif
                if %streql( $ngh_atype O.2 )
                    setvar count_O %set_or("$count_O" $ngh)
                endif
            endfor
            if %eq( %set_size("$count_H") 2 )
                setvar passed_set %set_or( $passed_set $count_H )
                setvar g_count[$level][NH2r] %math( $g_count[$level][NH2r] + 1 )
                setvar find_group TRUE
            endif
            if %eq( %set_size("$count_O") 2 )
                setvar passed_set %set_or( $passed_set $count_O )
                setvar g_count[$level][NO2] %math( $g_count[$level][NO2] + 1 )
                setvar find_group TRUE
            endif
        ;;
nitro NO2 group (Unity format)
        case N.2)
            setvar ngh %atom_info( $j neighbors )
            setvar ngh_left %set_diff( %set_create($ngh) $passed_set)
            setvar count_O
            for ngh in %set_unpack( "$ngh_left" )
                setvar ngh_atype %atom_info( $ngh type )
                if %or( %streql($ngh_atype O.2) %streql($ngh_atype O.3) )
                    setvar count_O %set_or("$count_O" $ngh)
                endif
            endfor
            if %eq( %set_size("$count_O") 2 )
                setvar passed_set %set_or( $passed_set $count_O )
                setvar g_count[$level][NO2] %math( $g_count[$level][NO2] + 1 )
                setvar find_group TRUE
            endif
        ;;
nitroso NO group
        case N.2)
            setvar ngh %atom_info( $j neighbors)
            setvar ngh_left %set_diff( %set_create($ngh) $passed_set )
            setvar count_O
            for ngh in %set_unpack( "$ngh_left" )
                setvar ngh_atype % atom_info( $ngh type )
                if %streql( $ngh_atype O.2)
                    setvar count_O %set_or( "$count_O" $ngh)
                endif
            endfor
            if %eq( %set_size("$count_O") 1 )
                setvar passed_set %set_or( $passed_set $count_O )
                setvar g_count[$level][NO] %math( $g_count[$level][NO] + 1 )
                setvar find_group TRUE
            endif
        ;;
nitrile/cyano CN group
        case C.1)
            setvar ngh %atom_info( $j neighbors)
            setvar ngh_left %set_diff( % set_create($ngh) $passed_set )
            if $ngh_left
                setvar ngh_atype %atom_info( $ngh_left type )
                if % streql( $ngh_atype N.1 )
                    setvar passed_set %set_or( $passed_set $ngh_left )
                    setvar g_count[$level][CN] %math( $g_count[$level][CN] + 1 )
                    setvar find_group TRUE
                endif
            endif
        ;;
carbonyl CO group
        case C.2)
            setvar ngh %atom_info( $j neighbors )
            setvar ngh_left %set_diff( %set_create($ngh) $passed_set)
            setvar count_O
            for ngh in %set_unpack( "$ngh_left" )
                setvar ngh_atype %atom_info( $ngh type )
                if %streql( $ngh_atype O.2)
                    setvar count_O %set_or( "$count_O" $ngh)
                endif
            endfor
            if %eq( %set_size("$count_O") 1 )
```

APPENDIX-continued

```
            setvar passed_set %set_or( $passed_set $count_O )
            setvar g_count[$level][CO] %math( $g_count[$level][CO] + 1 )
            setvar find_group TRUE
         endif
      ;;
sulfonyl SO2 group
      case S.o2)
         setvar ngh %atom_info( $j neighbors )
         setvar ngh_left %set_diff( %set_create($ngh) $passed_set )
         setvar count_O
         for ngh in %set_unpack( "$ngh_left" )
            setvar ngh_atype %atom_info( $ngh type )
            if %streql( $ngh_atype O.2)
               setvar count_O %set_or( "$count_O" $ngh )
            endif
         endfor
         if %eq( %set_size("$count_O") 2 )
            setvar passed_set %set_or( $passed_set $count_O )
            setvar g_count[$level][SO2] %math( $g_count[$level][SO2] + 1 )
            setvar find_group TRUE
         endif
      ;;
sulfinyl SO group
      case S.o)
         setvar ngh %atom_info( $j neighbors )
         setvar ngh_left %set_diff( %set_create($ngh) $passed_set)
         setvar count_O
         for ngh in %set_unpack( "$ngh_left" )
            setvar ngh_atype %atom_info( $ngh type )
            if %streql( $ngh_atype O.2 )
               setvar count_O %set_or( "$count_O" $ngh )
            endif
         endfor
         if %eq( %set_size("$count_O") 1 )
            setvar passed_set %set_or( $passed_set $count_O )
            setvar g_count[$level][SO] %math( $g_count[$level][SO] + 1 )
            setvar find_group TRUE
         endif
      ;;
hydroxyl OH group
      case O.3)
         setvar ngh %atom_info( $j neighbors )
         setvar ngh_left % set_diff( % set_create($ngh) $passed_set )
         if $ngh_left
            setvar ngh_atype %atom_info( $ngh_left type )
            if %streql( $ngh_atype H)
               setvar passed_set %set_or( $passed_set $ngh_left )
               setvar g_count[$level][OH] %math( $g_count[$level][OH] + 1 )
               setvar find_group TRUE
            endif
         endif
      ;;
      endswitch
      if %not( $find_group )
         setvar a_count[$level][$atype] %math( $a_count[$level][$atype] + 1 )
      endif
      setvar ngh %atom_info( $j neighbors )
      for k in $ngh
         if %not( %set_member($k $passed_set) )
            setvar atoms_at_level[$next_level]\
                  $atoms_at_level[$next_level] $k
#           setvar parent[$k] $j
            setvar passed_set %set_or($passed_set $k)
         endif
      endfor
   endfor
   setvar level %math($level + 1)
endwhile
# now calculate the prediction from the coefficients saved in <file>
setvar pka %read( $fhdr )
setvar line %read( $fhdr )
while %not( %eof( $fhdr ) )
   setvar coff % arg(1 $line)
   setvar x %arg(2 $line)
   setvar a_or_g %substr($x 1 1)
   setvar level %substr($x 3 1)
   setvar atype % substr($x 5)
   if %streql( $a_or_g "A" )
      if %not( %set_member( $atype $simple_types ) )
```

APPENDIX-continued

```
          setvar atype %cat(%substr($atype 1 1) "." %substr($atype 2))
        endif
        setvar pka %math( $pka + $coff * $a_count[$level][$atype] )
#       if %gt( $a_count[$level][$atype] 0 )
#         echo "$level, $atype, $a_count[$level][$atype]"
#       endif
      else
        setvar pka %math( $pka + $coff * $g_count[$level][$atype] )
#       if %gt( $g_count[$level][$atype] 0 )
#         echo "$level, $atype, $g_count[$level][$atype]"
#       endif
      endif
      setvar line %read( $fhdr)
    endwhile
    echo "Predicting pKa for $ma ( %mol_info($ma name) atom $N_atom): $pka"
    %rewind( $fhdr )
  endfor
endfor
#%file_delete( $tmpfile1 $tmpfile2) > $nulldev
%close( $fhdr )
default $old_default > $nulldev
```

We claim:

1. A software implemented methodology for determining the $pK_a$ of a molecule of interest comprising the following steps:

a) determine the hierarchical atom type connectivity tree noting the number of times each atom type occurs for each ionizable group on each molecule of a series of molecules for which an experimentally determined $pK_a$ is known;

b) place each of the determined atom types noting the number of times each atom type occurs for each hierarchically determined connectivity tree in a row of a data table along with the experimentally determined $pK_a$ of the molecule from which the tree was determined;

c) using the partial least squares (PLS) statistical methodology, extract coefficients associated with each atom type represented at each hierarchical level;

d) determine the hierarchical atom type connectivity tree noting the number of times each atom type occurs for the molecule of interest; and e) multiply the number of occurrences of each atom type in the molecule of interest by the PLS coefficient determined for that atom type and sum the resulting multiplications to obtain the predicted $pK_a$.

2. The method of claim 1 in which each atom type from the hierarchical atom connectivity tree in steps a and d for each ionizable group on each molecule is placed into a separate bin in a bit string.

3. The method of claim 2 in which the extracted coefficients are associated with the appropriate bin in the bit string.

* * * * *